United States Patent [19]

Hord et al.

[11] Patent Number: 5,338,549
[45] Date of Patent: Aug. 16, 1994

[54] POWDERED PSYLLIUM DRINK MIX COMPOSITIONS CONTAINING ANTIOXIDANT

[75] Inventors: Lee A. Hord, Mason; Robert E. Barron, Cincinnati, both of Ohio

[73] Assignee: The Procter & Gamble Company, Cincinnati, Ohio

[21] Appl. No.: 994,372

[22] Filed: Dec. 21, 1992

[51] Int. Cl.⁵ .................. A61K 35/78; A61K 9/14; A61K 9/16; A61K 31/725
[52] U.S. Cl. .................... 424/439; 424/490; 424/195.1; 514/892; 426/598; 426/629
[58] Field of Search .............. 424/440, 439, 195.1, 424/489, 493, 490; 524/892; 426/590, 598, 615, 629, 482

[56] References Cited

U.S. PATENT DOCUMENTS

| | | | |
|---|---|---|---|
| Re. 32,811 | 12/1988 | Rudin | 424/195.1 |
| 906,709 | 12/1908 | Heintz | 424/195.1 |
| 2,060,336 | 11/1936 | Near et al. | 99/131 |
| 3,148,114 | 9/1964 | Fahrenbach et al. | 167/55 |
| 3,455,714 | 7/1969 | Bishop et al. | 106/205 |
| 4,321,263 | 3/1982 | Powell et al. | 424/195 |
| 4,341,805 | 7/1982 | Chaudhary | 426/481 |
| 4,459,280 | 7/1984 | Colliopoulos et al. | 424/35 |
| 4,511,561 | 4/1985 | Madaus et al. | 424/195.1 |
| 4,548,806 | 10/1985 | Colliopoulos et al. | 424/35 |
| 4,551,331 | 11/1985 | Rudin | 424/195.1 |
| 4,557,938 | 12/1985 | Sander et al. | 426/453 |
| 4,565,702 | 1/1986 | Morley et al. | 426/93 |
| 4,619,831 | 10/1986 | Sharma | 426/93 |
| 4,639,367 | 1/1987 | Mackles | 424/45 |
| 4,731,246 | 3/1988 | Chavkin et al. | 424/195.1 |
| 4,737,364 | 4/1988 | Kalogris | 424/195.1 |
| 4,747,881 | 5/1988 | Shaw et al. | 106/209 |
| 4,784,861 | 11/1988 | Gori | 426/74 |
| 4,812,315 | 3/1989 | Tarabishi | 424/466 |
| 4,824,672 | 4/1989 | Day et al. | 424/195.1 |
| 4,828,842 | 5/1989 | Furst et al. | 424/480 |
| 5,173,296 | 12/1992 | Andre et al. | 426/660 |
| 5,178,896 | 1/1993 | Langner | 426/590 |

FOREIGN PATENT DOCUMENTS

| | | | |
|---|---|---|---|
| 105195 | 4/1984 | European Pat. Off. | A61L 2/06 |
| 144644 | 6/1985 | European Pat. Off. | A23L 1/308 |
| 285201 | 10/1988 | European Pat. Off. | A61K 35/78 |
| 323666 | 7/1989 | European Pat. Off. | A61K 31/785 |
| 412604 | 2/1991 | European Pat. Off. | A23L 1/00 |
| 2616329 | 12/1988 | France | A61K 35/78 |
| WO80/00658 | 4/1980 | PCT Int'l Appl. | A61K 9/00 |
| WO85/01441 | 4/1985 | World Int. Prop. O. | A61K 35/78 |

OTHER PUBLICATIONS

Physicians Desk Reference for Nonprescription Drugs, 10th Edition, pp. 641–642 (1989): "Orange Flavor Metamucil ®"; Strawberry Flavor Metamucil ®; Sugar Free Orange Flavor Metamucil ®; Sugar Free Lemon–Lime Flavor Effervescent Metamucil ®; Sugar Free Orange Flavor Effervescent Metamucil ®; sold by The Procter & Gamble Company.
Fybogel ® Orange, sold by Reckitt & Colman.
Sunrise Smooth Metamucil ® (Citrus and Orange Flavored; Regular and Sugar Free), sold by The Procter & Gamble Company.
Goodman and Gilman, The Pharmacologic Basis of Therapeutics, 6th Edition, 1004 and 1007 (1980).
Garvin et al., Proc. Soc. Exp. Biol. Med., 120, 744–746 (1965).
Forman et al., Proc. Soc. Exp. Biol. Med., 127, 1060–1063 (1968).
Anderson et al., Fed. Proc., 46, 877 (1987).
Anderson et al., Am. J. Gastroenterology, 81, 907–919 (1986).
Fagerberg, Curr. Ther. Res., 31, 166 (1982).
"Tenox ® Food–Grade Antioxidants", product brochure published by Eastman Chemical Company (1992).

*Primary Examiner*—Edward Webman
*Attorney, Agent, or Firm*—Kathleen M. Harleston; Kim William Zerby; Douglas C. Mohl

[57] ABSTRACT

Psyllium husk-containing powdered drink mix compositions comprising a free radical scavenging antioxidant material to reduce the incidence of vacuum generation in air tight containers and of off-odors.

6 Claims, No Drawings

POWDERED PSYLLIUM DRINK MIX COMPOSITIONS CONTAINING ANTIOXIDANT

BACKGROUND OF THE INVENTION

The present invention relates to psyllium husk-containing powdered drink mix compositions comprising an antioxidant. The present invention also relates to a method for reducing the creation of a vacuum in an air tight container filled with a psyllium-containing powdered drink mix composition.

Powdered drink mix products containing psyllium seed husk are known (for example, Metamucil®, sold by The Procter & Gamble Company). Such products are useful for the benefit of normalizing bowel function and laxation. In addition, recent research has demonstrated the effectiveness of psyllium seed husk fiber in reducing human serum cholesterol levels and in controlling blood glucose levels in diabetics.

Psyllium-containing drink mix products have been sold in plastic canisters and in individual packets for portable use. Random unopened canisters of such product develop a vacuum during storage, sometimes to the extent that the bottle is drawn in. More recent developments relating to reducing the particle size of the psyllium husk used in these powdered drink mix products has increased the incidence of this phenomenon.

It has been discovered that the addition of certain antioxidant materials to these compositions reduce the incidence of vacuum creation. They further provide the benefit of improved aesthetics associated with the odor of the product after storage. These benefits from adding antioxidant materials to psyllium-containing powdered drink mix compositions is surprising since psyllium husk is predominantly a polysaccharide-containing fiber material, which is not typically viewed as an oxidizable material. However, while not to be limited by theory, it is believed that the benefits observed for the present invention compositions is due to the ability of the antioxidant materials to inhibit oxidation of the very low levels of psyllium oil inherently present in psyllium husk.

It is therefore an object of the present invention to provide psyllium-containing powdered drink mix compositions having improved storage stability. In particular, it is an object to provide psyllium-containing drink mix compositions which do not create a vacuum when stored in an air-tight container and/or which does not generate off-odors during storage. A further object is to provide a method for reducing the creation of a vacuum in an air-tight container filled with a psyllium-containing powdered drink mix composition.

These and other objects of the present invention will become readily apparent from the detailed description which follows.

All percentages and ratios used herein are by weight unless otherwise specified. Screen mesh sizes used herein are based on U.S. standards.

SUMMARY OF THE INVENTION

The present invention relates to psyllium husk-containing powdered drink mix compositions. Such compositions comprise: (a) from about 10% to about 99% psyllium husk; (b) from about 1% to about 90% powdered drink mix carrier materials; and (c) a safe and antioxidant effective amount of a free radical scavenging antioxidant material; wherein further said composition is in a powdered form mixable with a liquid to form a suspension of the psyllium husk.

The present invention also relates to a method for reducing the creation of a vacuum in an air tight container filled with a psyllium-containing powdered drink mix composition. Said method comprises the steps of: (a) preparing a powdered psyllium drink mix composition comprising psyllium husk and a safe and antioxidant effective amount of a free radical scavenging antioxidant material; and (b) filling this powdered psyllium drink mix composition into an air tight container.

DETAILED DESCRIPTION OF THE INVENTION

The drink mix compositions of the present invention are psyllium-containing compositions in powdered form suitable for mixing with a liquid to form a psyllium husk suspension for oral consumption. The components of the compositions according to the present invention, and representative amounts, are described in detail as follows.

Psyllium Husk

The psyllium husk used in the present invention is from psyllium seeds, from plants of the *Plantago* genus. Various species such as *Plantago lanceolate, P. rugelii,* and *P. major* are known. Commercial psyllium husk include the French (black; *Plantago indica*), Spanish (*P. psyllium*) and Indian (blonde; *P. ovata*). Indian (blonde) psyllium husk is preferred for use herein. Also preferred is psyllium husk which is at least about 85% pure, more preferably at least about 90% pure, and most preferably at least about 95% pure.

The psyllium husk is obtained from the seed coat of the psyllium seeds. It is typical to remove the seed coat from the rest of the seed by, for example, slight mechanical pressure, and then to use only the seed coat. The seed coat is preferably removed and sanitized by methods known in the art. Preferred is sanitized psyllium seed husk having substantially intact cell structure, the sanitization having been accomplished by methods such as ethylene oxide sanitization and superheated steam sanitization (as taught in U.S. Pat. No. 4,911,889, issued Mar. 27, 1990 to Leland et. al., the disclosures of which are incorporated herein by reference in their entirety). It is also preferred that the psyllium husk herein has reduced particle size.

Preferred psyllium husk utilized in compositions of the present invention has a substantial amount of small particle size psyllium husk such that the psyllium husk comprises psyllium husk particle sizes distributed to have more than about 90% smaller than about 45 mesh. More preferably, more than about 80% is smaller than about 50 mesh, further preferred is more than about 80% is smaller than about 60 mesh, and most preferably at least about 80% is smaller than about 80 mesh. Further preferred particle sizes are distributed as follows: less than about 25% larger than about 60 mesh, and at least about 40% smaller than about 80 mesh. More preferred are particle size distribution of: less than about 10% larger than about 60 mesh, at least about 40% within the range of from about 80 mesh to about 200 mesh, and less than about 50% smaller than about 200 mesh. Particle sizes and particle size distributions may be readily determined by one of ordinary skill in the art, for example by sieving using an Alpine Laboratory Air Jet Sieve, Type 200 LS (sold by Alpine American Corp., Natick Mass.).

The drink mix compositions preferably contain from about 10% to about 99%, more preferably from about 20% to about 90%, most preferably from about 25% to about 75%, of psyllium husk.

Free Radical Scavenging Antioxidant Materials

"Free radical scavenging antioxidant materials", as used herein, means those materials which act to prevent oxidation in ingestible products by functioning as free radical scavengers. Preferred free radical scavenging antioxidant materials are selected from the group consisting of tert-butyl-hydroquinone ("TBHQ"), propyl gallate, butylated hydroxytoluene ("BHT"), butylated hydroxyanisole ("BHA"), octyl gallate, dodecyl gallate, tocopherols (e.g., Vitamin E), Rosmarinus officinalis (Rosemary extract), Tempeh oil, and mixtures thereof. Preferred are BHT, BHA, TBHQ and propyl gallate. It is to be recognized that for purposes of the present invention, materials otherwise useful as antioxidants which do not act as free radical scavengers, such as those materials which function solely by chelating metals which can initiate oxidation reactions (e.g., citric acid), are not "free radical scavenging antioxidant materials" herein, but may be acceptable optional powdered drink mix carrier materials as described in more detail hereinafter.

The term "safe and antioxidant effective amount", as used herein, means an amount of a free radical scavenging antioxidant material safe for human oral consumption and effective for reducing the rate of oxidation of the psyllium-containing compositions according to the present invention. Levels of free radical scavenging antioxidant materials to be used in ingestible products are known in the art. The free radical scavenging antioxidant material is typically present in the compositions according to the present invention within the range of from about 1 ppm to about 1%, preferably from about 1 ppm to about 0.1%, and most preferably from about 1 ppm to about 0.02%. It is further preferred that the free radical scavenging antioxidant material be in contact with the psyllium husk, especially by coating the psyllium with a coating comprising some or all of the free radical scavenging antioxidant material.

Powdered Drink Mix Carrier Materials

Powdered drink mix carrier materials useful for the compositions of the present invention must be safe for oral administration to humans, and may be chosen by one of ordinary skill in the art as appropriate for the powdered drink mix form and use intended for the product. Psyllium-containing powdered drink mix products, methods for making, and carrier materials useful for these products, are described more fully, for example, in Colliopoulos et al. U.S. Pat. No. 4,459,280, issued Jul. 10, 1984; Colliopoulos et al. U.S. Pat. No. 4,548,806, issued Oct. 22, 1985; Powell et al. U.S. Pat. No. 4,321,263, issued Mar. 23, 1982; and Furst et al. U.S. Pat. No. 4,828,842, issued May 9, 1989; all of which are incorporated by reference herein in their entirety. The powdered drink mix compositions of the present invention comprise from about 1% to about 90%, preferably from about 10% to about 80%, and more preferably from about 25% to about 75%, of powdered drink mix carrier materials.

Preferred powdered drink mix carrier materials for such powder forms are known and are also described in detail, for example, in U.S. Pat. Nos. 4,459,280 and 4,548,806, incorporated hereinbefore by reference. Preferred are such powders (preferably sugar free) comprising maltodextrin. Also especially preferred are powders comprising agglomerates of psyllium and/or coated psyllium, especially agglomerated with maltodextrin and/or sucrose.

Agglomerating materials preferred for use herein are therefore known. These agglomerating materials include those selected from the group consisting of water dispersible hydrolyzed starch oligosaccharide, monosaccharide, di-saccharide, polyglucose, polymaltose, and mixtures thereof. Compositions of the present invention preferably comprise from about 0.5% to about 20% of agglomerating material coating on said psyllium husk, preferably from about 1% to about 10%, and more preferably from about 1% to about 5%.

Hydrolysis of starch may be accomplished by a reaction of either acid, enzymes (e.g., alpha-amylase, beta-amylase or amyloglucosidase), or a combination of the two either together or reacted in series. The hydrolysis will follow different pathways depending on whether acids or enzymes are used. The result is a mixture of oligosaccharides which may be separated for their different properties. The resulting separated water dispersible (preferably soluble) hydrolyzed starch oligosaccharides are classified by their reducing sugar content, i.e., the mono- or di-saccharides such as glucose or fructose. The percent reducing sugar content in the particular hydrolyzed starch oligosaccharide is measured on a weight/weight basis as the Dextrose Equivalent (or "D.E."). Hydrolyzed starch oligosaccharides with a D.E. of from 0 to 20 are called maltodextrins. The solid maltodextrins have low to moderate sweetness, low to moderate hygroscopicity, solubility in water and alcohol, and have reduced browning. Above a D.E. of about 20 the hydrolyzed starch oligosaccharides are called syrup solids. The syrup solids are soluble but have a more noticeable sweetness and are more hydroscopic. Above a D.E. of about 30, the syrup solids become less desirable for use herein. A preferred water dispersible hydrolyzed starch oligosaccharide therefore has a D.E. of from about 0 to about 30. A preferred maltodextrin has a D.E. of from about 5 to about 20, more preferably about 10 (i.e., a reducing sugar content ratio of 10% w/w of the oligosaccharide).

The mono-saccharides are those carbohydrates that in general are aldehyde-alcohols or ketone alcohols that are a hexose or pentose and have a sweet taste. They are readily soluble in water and form crystalline solids. Di-saccharides are carbohydrates which yield two mono-saccharides on hydrolysis. Examples of di-saccharides are lactose, sucrose and maltose.

Preferred compositions of the present invention comprise an amount of edible, water soluble salt sufficient to reduce the gellation rate of the drink mix composition relative to the compositions without added salt. The term "edible, water soluble salts" as used herein, means any salt material, organic or inorganic, which is soluble in water (under normal use conditions for a psyllium-containing drink mix composition) and having a pKa of greater than about 5, and which is safe for ingestion by humans. Examples of edible, water soluble salts include magnesium sulfate, calcium chloride, calcium sulfate, potassium chloride, sodium chloride, potassium sulfate, sodium sulfate, zinc chloride, zinc sulfate, potassium sorbate, and mixtures thereof. Preferred are the salts of divalent cations (e.g. calcium, magnesium, zinc) and especially those salts of strong inorganic acids (e.g., magnesium sulfate, calcium sulfate, calcium chloride, zinc sulfate, zinc chloride, and mixtures thereof).

Determination of whether the level of salt present in a psyllium husk-containing powdered drink mix composition is a level whereby the gellation rate of the psyllium-containing drink mix composition in an aqueous solution is reduced is readily made by simple experimentation, e.g. by comparing the rate of viscosity increase for a composition containing the salt versus the composition containing the same components but not the edible, water soluble salt. Methods and equipment for measuring gellation rates and viscosity of liquids are known, and such measurements and determinations can easily be made by one skilled in the art. (For example, a Brinkmann Viscometer may be used.)

Compositions of the present invention therefore may comprise from about 0.1% to about 50% edible, water soluble salts, preferably from about 0.1% to about 20%, and more preferably from about 0.5% to about 5% by weight of the drink mix composition.

Preferred compositions of the present invention also comprise as part or all of the optional carrier material an edible acid. The term "edible acids", as used herein, means any water soluble acid material having a $PK_a$ of less than about 5, preferably within the range of from about 2 to about 5, and is safe for ingestion by humans. Examples of edible acids include, but are not limited to, citric acid, ascorbic acid, malic acid, succinic acid, tartaric acid, phosphoric acid, monopotassium phosphate, and mixtures thereof. Preferred are ascorbic acid, phosphoric acid, malic acid, and citric acid, with citric acid being most preferred.

The compositions of the present invention typically comprise from about 0.1% to about 25% edible acid, preferably from about 0.1% to about 10%, and more preferably from about 0.1% to about 5%. Also preferred are compositions containing less than about 2% edible acid, more preferably less than about 1% edible acid, and most preferably less than about 0.5% edible acid.

Preferred compositions of the present invention are those which have some or all of the edible acid and/or edible, water soluble salt coated on the psyllium husk, and further preferably such that the psyllium husk is agglomerated. Preferred single layer coating of the psyllium husk is achieved by utilizing equipment (referred to herein as single pass fluidizing powder wetting apparatus) which operates preferably by dropping a dry blend psyllium-containing material through a highly turbulent annular zone formed by a cylindrical wall and a rotating shaft with variously pitched attached blades. A solution containing edible acid and/or edible, water soluble salt, preferably also containing the free radical scavenging antioxidant material, is preferably sprayed into this zone to contact a dry psyllium-containing blend. The resulting coated, preferably agglomerated, psyllium husk is dropped to a fluid bed dryer where the added solvent is removed. An example of this equipment is the Bepex Turboflex Model No. TFX-4 (sold by Bepex Corporation; Minneapolis, Minn.) with a six square foot bed vibrating fluid bed dryer (sold by Witte Corporation, Inc.; Washington, N.J.).

The psyllium-containing blend preferably comprises from about 25% to about 100% of psyllium. Optional components for the psyllium-containing blend include, but are not limited to, edible acid, sweetening agents (preferably low calorie sweetening agents), coloring agents, agglomerating materials (especially maltodextrin), dietary fibers such as brans (e.g., wheat bran; oat bran; rice bran) and/or pharmaceutical agents (e.g., aspirin; non-steroidal antiinflammatories; sennosides). The salt may also be included in the psyllium-containing blend. As noted hereinbefore, it is preferred that the psyllium-containing blend be dry, but it is possible to utilize suitable solvents (e.g., alcohols and/or water) if one is careful, especially if water is utilized, not to cause substantial hydration and swelling of the psyllium, since this is expected to adversely affect the rate at which psyllium husk can interact with water or other fluids.

The solution mixture preferably comprises one or more edible acids and/or edible, water soluble salt to be sprayed onto the psyllium-containing blend along with also preferably comprising some or all of the free radical scavenging antioxidant materials. This may be prepared by selecting a liquid (e.g., alcohol and/or water) as appropriate for the materials being coated onto the psyllium husk. However, it is preferred that water be utilized. Preferred is also spraying the solution mixture onto a dry psyllium-containing blend. Preferably, when a spraying technique is used, the solution mixture is an aqueous solution comprising in addition to the free radical scavenging antioxidant material, from about 0% to about 50% (preferably from about 10% to about 25%) of the edible, water soluble salt and also from about 0% to about 50% (preferably from about 1% to about 20%) of edible acid. It is also optionally possible to repeat the coating and drying steps, thereby building up a coating on the psyllium husk which comprises several thin layers of the materials. In addition, other optional materials may be present in the solution mixture, such as coloring agents, pharmaceutical agents, and mixtures thereof.

Other methods for preparing compositions according to the present invention include dry blending the ingredients and other means of multiple layer coating of the psyllium husk. The latter may be accomplished by using, for example, fluid bed agglomerating equipment such as the Fluid Air, Inc. Model 0300 Granulator-Dryer.

Further, the preferred drink mix compositions of the present invention are unflavored. It is possible to include with such preferred compositions sweetening agents, preferred being low calorie sweetening agents including, but not limited to, aspartame, saccharin, cyclamate, acesulfame, and mixtures thereof. Further, it is possible to use such compositions as reduced flavor or non-flavored base formulations to make flavored compositions by adding flavoring agents.

The present invention compositions are useful for providing laxation and regulating bowel function for a human in need of such treatment. This comprises administering to a human in need of such treatment a safe and effective amount of a psyllium-containing composition of the present invention. Ingestion of from about 2.5 grams to about 30 grams per day of the psyllium fiber in a composition according to the present invention is appropriate in most circumstances to produce laxation. However, this can vary with the size and condition of the patient, and such matters will, of course, be apparent to the attending physician. However, since the psyllium material is nontoxic, even higher ingestion levels can be used without undue side effects. A typical dose for laxation purposes involves administering from about 3 to about 15 grams of psyllium fiber in one dose.

The present invention compositions are also useful for reducing serum cholesterol levels in humans. This comprises orally administering to a human in need of having a lowered blood cholesterol level a safe and effective amount of an aqueous liquid suspension of a psyllium-containing composition of the present invention. Ingestion of compositions of the present invention comprising amounts sufficient to administer from about 2.5 grams to about 30 grams per day of psyllium fiber, preferably from about 5 grams to about 15 grams, is appropriate in most circumstances. However, this can vary with the size and condition of the patient, and the patient's blood cholesterol level. Such matters will, of course, be apparent to the attending physician. However, since the psyllium material is nontoxic, even higher ingestion levels can be used without undue side effects, keeping in mind the materials herein have the hereinbefore noted laxative effect.

Treatment of the patient to reduce serum cholesterol levels comprises chronic ingestion in order to lower and maintain the lowered cholesterol levels. Daily ingestion is preferred, and a daily ingestion of from about 5 grams to about 15 grams of the psyllium fiber is most commonly used, with said ingestion preferably being at 2 or 3 regularly spaced intervals throughout the day. Again, depending on the patient's size and cholesterol level in the patient's blood, this can be varied.

The present invention also relates to a method for reducing the creation of a vacuum in an air tight container filled with a psyllium-containing powdered drink mix composition. Said method comprises preparing a powdered psyllium drink mix composition comprising psyllium husk and a safe and antioxidant effective amount of a free radical scavenging antioxidant material, and then filling this powdered psyllium drink mix composition into an air tight container.

The following example further describes and demonstrates an embodiment within the scope of the present invention. This example is given solely for the purpose of illustration and is not to be construed as limitations of the present inventions as many variations thereof are possible without departing from the spirit and scope of the invention.

EXAMPLE 1

| Components | Weight % |
|---|---|
| Psyllium[1] | 56.73 |
| Maltrin[2] | 40.72 |
| Magnesium Sulfate | 2.20 |
| Citric Acid | 0.35 |
| Tenox S-1[3] | 0.0017 |

[1] Psyllium husk of particle size 100% through 80 mesh.
[2] Maltodextrin
[3] A solution containing propyl gallate (20%), citric acid (10%) and propylene glycol (70%); sold by Eastman Chemical Company.

This psyllium drink mix composition according to the present invention is prepared by agglomerating by spraying a dry blend of the psyllium husk and maltrin with an aqueous solution of magnesium sulfate, citric acid, Tenox S-1 in a single pass agglomerator (as described in detail in European Patent Publication No. 412,604, published Feb. 13, 1991, the disclosures of which are incorporated herein by reference in their entirety) and subsequently dried in a fluidized bed dryer. Consumption of one teaspoon of this composition as a suspension in 8 ounces of water is effective for providing laxation for a patient in need of such benefit.

What is claimed is:

1. A psyllium husk-containing powdered drink mix composition comprising:
   (a) from about 20% to about 90% psyllium husk;
   (b) from about 10% to about 80% powdered drink mix carrier material selected from the group consisting of water dispersible hydrolyzed starch oligosaccharide, monosaccharide, disaccharide, polyglucose, polymaltose and mixtures t hereof;
   (c) from about 1 ppm to about 0.02% of a free radical scavenging antioxidant material selected from the group consisting of tert-buty-hydroquinone, propyl gallate, butylated hydroxytoluene, butylated hydroxyanisole, and mixtures thereof, said antioxidant material being in contact with the psyllium husk by coating the psyllium husk with a coating comprising some or all of the antioxidant material; and wherein further said composition is in a powdered from mixable with a liquid to form a suspension of the psyllium husk.

2. The composition according to claim 1 wherein the psyllium husk comprises psyllium husk particle sizes distributed to have more than about 80% smaller than about 50 mesh.

3. The composition according to claim 2, wherein the free radical scavenging antioxidant material is propyl gallate.

4. A method for reducing the creation of a vacuum in an air tight container filled with a psyllium-containing powdered drink mix composition, said method comprising the steps of:
   a) preparing a powdered psyllium drink mix composition comprising psyllium husk and a safe and antioxidant effective amount of a free radical scavenging antioxidant material selected from the group consisting of tert-butyl-hydroquinone, propyl gallate, butylated hydroxytoluene, butylated hydroxyanisole, octyl gallate, dodecyl gallate, tocopherols, Rosmarinus officinalis, tempeh oil, and mixtures thereof: wherein the antioxidant material is in contact with the psyllium husk by coating the psyllium husk with a coating comprising some or all of the antioxidant material; and
   (b) filling this powdered psyllium drink mix composition into an air tight container.

5. The method according to claim 4 wherein the free radical scavenging antioxidant material is selected from the group consisting of tert-butyl-hydroquinone, propyl gallate, butylated hydroxytoluene, butylated hydroxyanisole, and mixtures thereof.

6. The method according to claim 4 wherein the antioxidant material comprises propyl gallate.

* * * * *